United States Patent [19]

Suga

[11] Patent Number: 5,441,978

[45] Date of Patent: Aug. 15, 1995

[54] COMPOUND AND NEMATICIDE AGAINST PINE WOOD NEMATODES CONTAINING THE SAME

[75] Inventor: Takayuki Suga, Hiroshima, Japan

[73] Assignee: Kioritz Corporation, Tokyo, Japan

[21] Appl. No.: 12,589

[22] Filed: Feb. 3, 1993

[30] Foreign Application Priority Data

Feb. 7, 1992 [JP] Japan .................. 4-022204

[51] Int. Cl.⁶ ............... A61K 31/365; C07D 309/30
[52] U.S. Cl. ..................... 514/460; 549/292
[58] Field of Search .......... 549/292; 514/460

[56] References Cited

FOREIGN PATENT DOCUMENTS 63-104905  5/1988  Japan .
63-159302  7/1988  Japan .
63-264510  11/1988  Japan .
3-52805    3/1991  Japan .

OTHER PUBLICATIONS

Chem. Pharm. Bull. 40(5) 1130 (1992), Mohammad Ahad Ali et al. "Synthesis and Nematocidal Activity of Hydroxystilbenes".
Chemical Abstracts 78, 48(1973) 155087t; Gibbs, J. N.
Chemical Abstract 88, 134(1978) 16230w; Gorham, John.
Chemical Abstracts 111, 434(1989) 171162u, Koichiro et al.

Primary Examiner—C. Warren Ivy
Assistant Examiner—Ba K. Trinh
Attorney, Agent, or Firm—David G. Conlin; George W. Neuner

[57] ABSTRACT

A novel compound having nematicidal effect on pine wood nematodes which has the following structural formula:

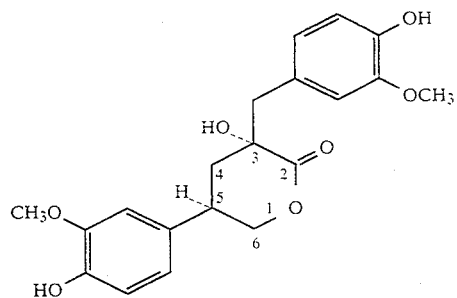

and a nematicide containing the compound described above against the pine wood nematodes.

6 Claims, 1 Drawing Sheet

COMPOUND AND NEMATICIDE AGAINST PINE WOOD NEMATODES CONTAINING THE SAME

BACKGROUND OF THE INVENTION

The present invention relates to a novel compound having a nematicidal effect on pine wood nematodes (*Bursaphelenchus xylophilus* Mamiya and Kiyohara) which is extracted from a pine tree, and a nematicide against the pine wood nematodes containing the same.

As well known, the pine wood nematode, fungivorous nematode, enters pine wood tissues and propagate to cause the pine trees to die.

The mechanism by which the pine wood nematodes cause the pine trees to die is considered as follows:

a) In the pine trees infected with the pine wood nematodes are prduced toxins (phytoalexins) such as benzoic acid (1), catechol (2), dihydroconiferyl alcohol (3), 8-hydroxycarvotanacetone (4) and 10-hydroxyverbenone (5), b) The nematodes secrete cellulase, c) Tracheids of the pine trees are clogged with α-pinene and β-pinene abnormally accumulated after the nematode infection, and d) Toxins are secreted by molds which propagate in the pine trees after the nematode infection.

The pine wood nematodes are transmitted to the pine trees through injurious insects such as a pine sawyer (*Monochamus alternatus* Hope).

Previous methods for preventing pine trees from dying by the pine wood nematodes mainly include (1) Cutting down damaged trees to exterminate ova, pupae and adults present in the damaged trees before the pine sawyers carrying nematodes, which are directly responsible for the death of the pine trees, escape from the damaged trees, and (2) the insecticide application methods (sprinkling and cropdusting) for preventing maturing feeding after eclosion and escape of the pine sawyers. The insecticides used herein include organic phosphorus pesticides, NAC agents (1-naphthyl-N-methylcarbamate), PAP agents (ethyl dimethyldithiophosphorylphenylacetate), EDB agents (1,2-dibromoethyl), MPP agents (O,O-dimethyl-O-[3-methyl-4-(methylthio)phenyl]thiophosphate) and MEP agents (dimethyl(3-methyl-4-nitrophenyl) thiophosphate).

In addition to the above-mentioned insecticides for the pine sawyers, nematicides for directly exterminating the pine wood nematodes in pine trees include a levamisole hydrochloride agent containing levamisole hydrochloride as a main insecticidal ingredient (trade name: "Century", Mitsubishi Petrochemical Co. LTD., Japan), a mesulfenfos agent (trade name: "Nemanon", Nihon Bayer Agro Chem K/K, Japan) and a morantel tartarate agent (trade name: "Greenguard", Fizer Pharmaceuticals INC., Japan).

The previous methods for exterminating the pine sawyers have the following problems:

(1) A great deal of labor is required.

(2) It is difficult to decide the suitable time of insecticide application because the time of eclosion and escape of the pine sawyers differs from year to year.

(3) The effectiveness of the insecticides has recently become lowered.

(4) In order to achieve the exterminating effect in forests and fields, the dosage per unit area is required to be 10 times that generally used in agriculture.

(5) Social problems such as the remaining of the given insecticides in soil, the remaining in water systems and the effect on ecosystems such as surrounding animals and plants are encountered.

The sufficient exterminating effect can not be attained because of these problems.

(6) The previous synthetic nematicide for directly exterminating the pine wood nematodes in wood are effective, but have a problem in safety because of their toxicity.

In contrast, it is unknown at all that a novel compound of the present invention isolated from an organic solvent extract from a pine tree is effective as a nematicide against the pine wood nematodes.

SUMMARY OF THE INVENTION

As a result of intensive studies on the extermination of pine wood nematodes, the present inventor discovered that a Formosan masson pine (*Pinus massoniana* Lamb.) contained a novel compound having a nematicidal activity against the pine wood nematodes, and that the compound had no problem in its safety, thus completing the present invention.

The present invention provides (1) a novel compound having the following structural formula:

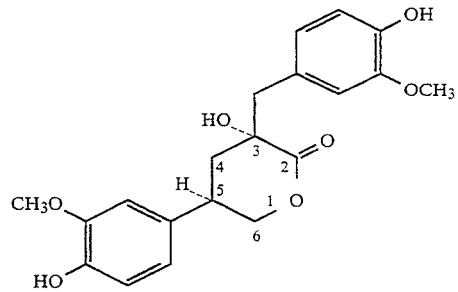

and (2) a nematicide for controlling the pine wood nematodes containing the compound described in (1).

DESCRIPTION OF THE PREFERRED EMBODIMENTS

Figure 1:
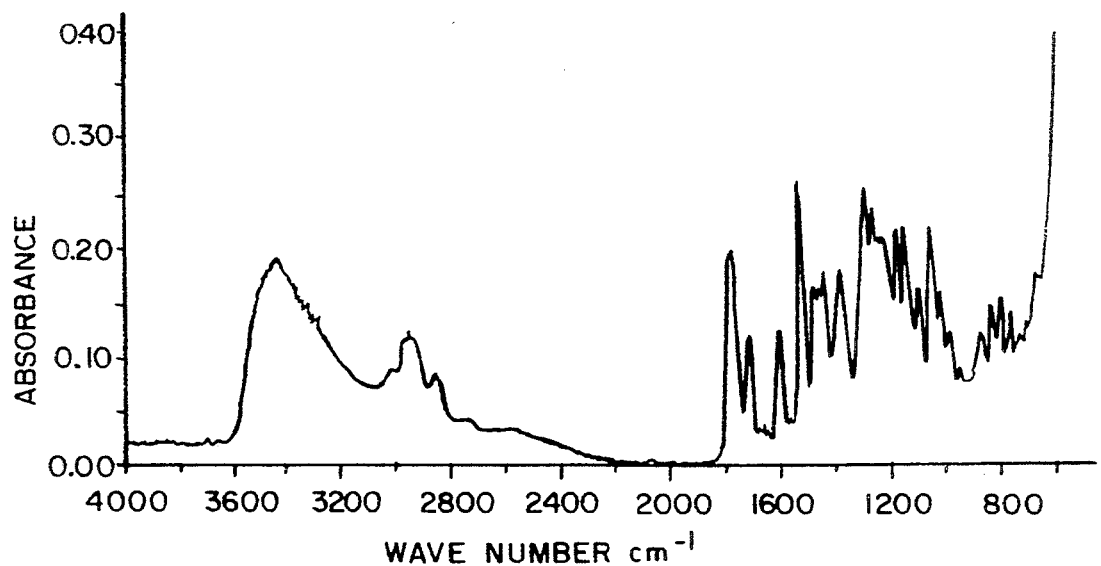
FIG. 1 shows an infrared absorption spectrum of the novel compound of the present invention.
Figure 2:
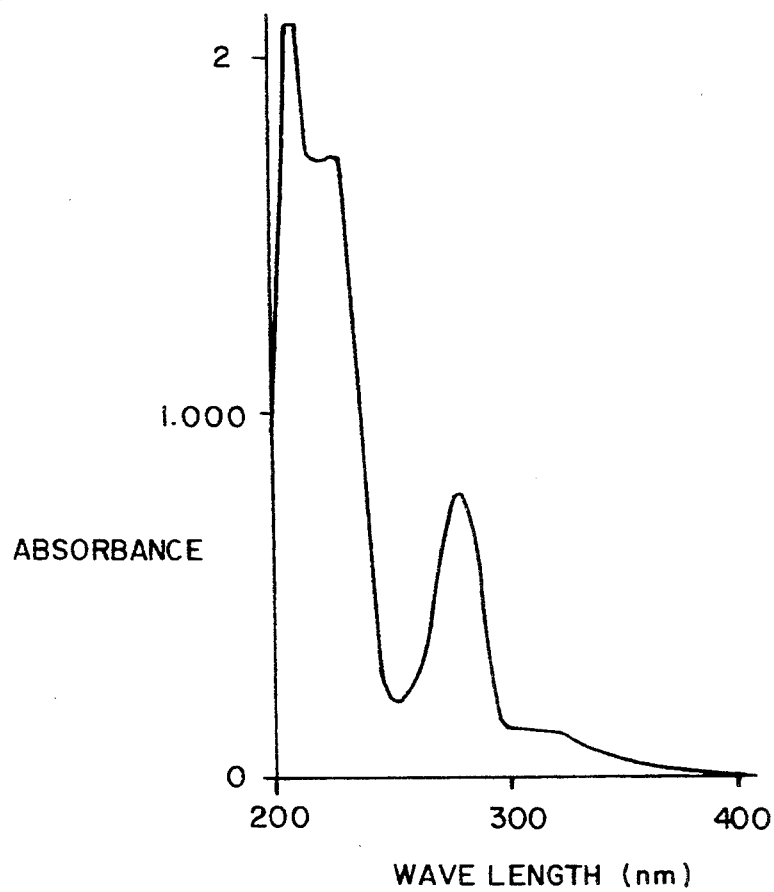
FIG. 2 shows an ultraviolet absorption spectrum of the novel compound of the present invention.

The novel compound of the present invention is obtained in the following manner.

The heart wood of Formosan masson pines is immersed in methyl alcohol, followed by filtration to give a methyl alcohol solution. Pentane is added to the resulting solution, and mixed with shaking. Then, a methyl alcohol layer is separated from a pentane layer. The methyl alcohol layer is distilled under reduced pressure to remove the solvent, and then the residue is dissolved in water. Ethyl acetate is added to the resulting aqueous solution, and mixed with shaking. Then, an aqueous layer is separated from an ethyl acetate layer. Then, butanol is added to the aqueous layer, followed by mixing with shaking to obtain a butanol solution. The resulting butanol solution is concentrated under reduced pressure to give a butanol-soluble fraction.

The butanol-soluble fraction thus obtained is subjected to gel filtration chromatography, silica gel chromatography, and subsequently preparative high performance liquid chromatography to isolate a novel compound. The resulting compound is yellow and oily, and has an optical rotation $[\alpha]_D{}^{25}$ of $-3.87°$ (c 0.062, MeOH) and a molecular weight of 374.1320 (theoretical value: 374.1364). This compound was confirmed to be [(3R,5S)-3-hydroxy-3-(4-hydroxy3-methoxybenzyl)-5-(4-hydroxy3-methoxyphenyl)-3,4,5,6-tetrahydro-2H-pyran-2-one] by an infrared absorption spectrum, an ultraviolet absorption spectrum and nuclear magnetic resonance analysis, and named "Massoniana lactone".

This novel compound of the present invention is considered to have three kinds of stereoisomers shown below, which are also expected to have nematicidal activity against the pine wood nematodes.

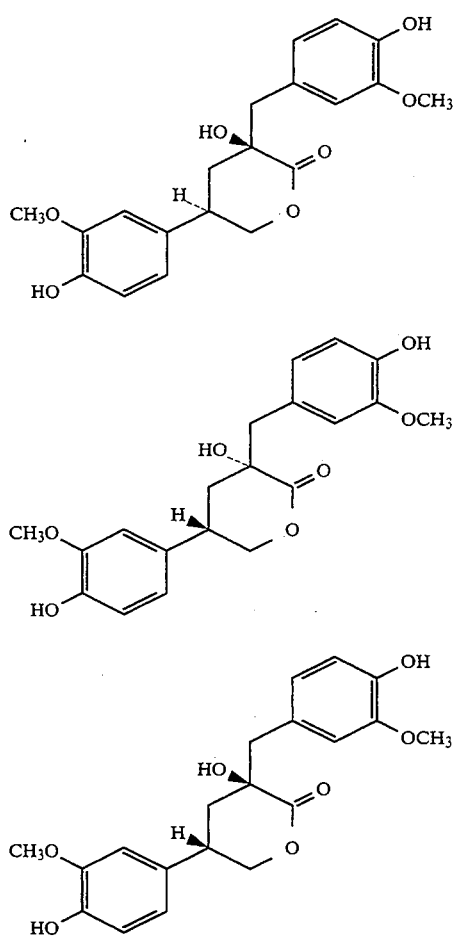

The nematicidal activity against propagative pine wood nematodes was tested for this novel compound, "Massoniana lactone". The results are given in Table 1.

The nematicidal activity test was conducted according to the following method:

1) About 300 propagative pine wood nematodes (all stages) incubated on the colony of *Botorytis cinerea* were placed in a plastic petri dish for counting (having a diameter of 5.5 cm).
2) The samples were dissolved in 2% ethanol solutions to concentrations 1,000 ppm, 100 ppm and 10 ppm, respectively, to prepare test solutions.
3) 4 ml of each test solution was poured into the above-mentioned petri dish in which the nematodes were placed. As a control solution, a 2% ethanol solution in which the sample was not dissolved was used.
4) The test solutions were allowed to stand at 10° C. in the dark, and the number of the moving nematodes was counted under a stereoscopic microscope every 24 hours for 3 days, thereby determining the survival rate. For each of the solutions, the test was repeated 5 times under the same conditions, and the mean value was determined therefrom to take it as the mean survival rate. In this case, the mean survival rate of the nematodes in the control test solution was 99.5% and the standard error thereof was ±3% at any time.
5) The nematicidal activity was indicated by the relative lethal rate. The relative lethal rate was determined by the following equation:

$$\text{Relative lethal rate (\%)} = 100 - \frac{\text{Mean survival rate in sample solution}}{\text{Mean survival rate in control solution}} \times 100$$

TABLE 1

| Nematicidal activity against the propagative pine wood nematodes | | | |
|---|---|---|---|
| | Relative lethal rate (%) 100 ppm | | |
| | After 1 day | After 2 days | After 3 days |
| Novel compound, "Massoniana lactone" | 37.5 | 66.5 | 81.9 |
| Agricultural chemical, "Century" | 88.5 | 89.4 | 91.6 |

As apparent from Table 1, the novel compound of the present invention, "Massoniana lactone", has nematicidal activity against the pine wood nematodes.

The nematicides containing this novel compound, "Massoniana lactone", having the nematicidal activity, Massoniana lactone, as a main ingredient contain this active ingredient in an amount of about 1 to 10%, in combination with another known carrier, etc.

As the carriers of the nematicides for the pine wood nematodes, liquid carriers or solid carriers are used depending on the purpose of their use.

The liquid carriers include water, alcohols, ketones, ethers, aromatic hydrocarbons, acid amides and esters. The solid carriers include known solid carriers such as mineral powders, alumina, sulfur powder and active carbon.

For the formulation, the nematicides can be used as injection and application agents. These preparations may contain emulsifiers, suspensions, stabilizers, stickers, penetrants and dispersing agents, if necessary, and can be prepared by methods known in the art.

The following example is given by way of illustration and is not to be construed as a limitation of the invention.

EXAMPLE

The heart wood (34 kg) of Formosan masson pines was immersed in methyl alcohol (about 30 liter) for 3 months, followed by filtration to obtain a methyl alcohol solution (20 liter). Then, pentane was added to the resulting methyl alcohol solution in an amount of 400 ml per liter of methyl alcohol solution, and mixed in a separating funnel with shaking for 30 minutes. Then, a methyl alcohol layer was separated from a pentane layer. The methyl alcohol layer was distilled under reduced pressure to remove the solvent, and then the residue was dissolved in water (2 liter). Ethyl acetate (600 ml) was added to the resulting aqueous solution, and mixed in a separating funnel with shaking for 30 minutes. An aqueous layer was separated from an ethyl acetate layer. Then, butanol (600 ml) was added to the aqueous layer, followed by mixing with shaking to give a butanol solution. The resulting butanol solution is concentrated under reduced pressure to give a butanol-soluble fraction (24 g).

The butanol-soluble fraction thus obtained was subjected to gel filtration chromatography, silica gel chromatography, and subsequently preparative high performance liquid chromatography to isolate a novel compound (2 mg). The resulting compound has the following properties:

Yellow and oily; $[\alpha]_D^{25}$ −3.87° (c 0.062, MeOH)

SI MS, m/z 397 (M$^+$ +Na)

High resolution EIMS, found value: m/z 374.1320 (M$^+$)

expected value: 374.1364

($C_{20}H_{22}O_7$)

CD; $\Delta\epsilon$ (234 nm) = −1.20 (c 0.0002449 mol/l, MeOH)

IR (KBr); 3400, 1920, 1760, 1695, 1600 cm$^{-1}$

UV (MeOH); 324($\epsilon$440), 282(3,170), 228(7,020), 210(10,050) nm $^1$H NMR (500 MHz, acetone-d$_6$); $\delta$2.43(1H,m), 2.48(1H, dd,J=9.6,13.3 Hz), 2.79(1H,dd,J=4.6,13.3 Hz), 2.84(1H,d,J=13.7 Hz), 3.12(1H,d,J=13.7 Hz), 3.79(3H,s), 3.82(3H,s), 6.57(1H,dd,J=2.3,8.2 Hz), 6.59(1H,dd, J=2.3,8.2 Hz), 6.66(1H,d,J=2.3 Hz), 6.68(1H,d,J=2.3 Hz), 6.69(1H,d,J=8.2 Hz), 6.70(1H,d,J=8.2 Hz) $^{13}$C NMR (125 MHz, acetone-d$_6$); $\delta$32.2(CH$_2$), 41.8(CH$_2$), 44.6(CH), 56.4(CH$_3$—Ox2), 71.8(CH$_2$—O), 77.4(C—O), 113.5(CH), 114.9(CH), 116.1(CH), 116.2(CH), 122,3(CH), 124.0(CH), 128.2(C), 131.9(C), 146.1(C), 146.7(C), 148.8(C), 149.0(C), 180.6(C=O)

This compound has the following structural formula, and is [(3R, 5S)-3-hydroxy-3-(4-hydroxy3-methoxybenzyl)-5-(4-hydroxy3-methoxyphenyl)-3,4,5,6-tetrahydro-2H-pyran-2-one], which is named "Massoniana lactone".

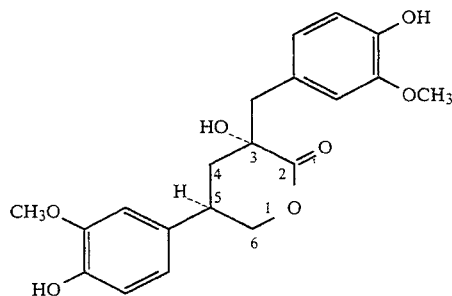

About 1 to 10% of the resulting novel compound, "Massoniana lactone", is dissolved in a 2% alcoholic solvent, and the solution was enclosed in ampoules to prepare an injection formulation with which tracheids of pine trees are injected.

What is claimed is:

1. A isolated compound having the following structural formula:

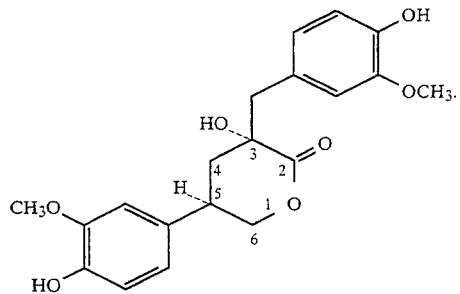

2. A nematicide composition having activity against pine wood nematodes, said composition containing in an alcoholic solution the compound claimed in claim 1.

3. Isolated (3R, 5S)-3-hydroxy-3-(4-hydroxy-3-methoxybenzyl)-5-(4-hydroxy-3-methoxyphenyl)-3,4,5,6-tetrahydro-2H-pyran-2-one having the infrared absorption spectrum of FIG. 1.

4. A nematicide composition comprising in a solvent about 1 to 10% by weight of the compound of claim 3.

5. A nematicide composition comprising about 1 to 10% by weight of the compound of claim 1.

6. Isolated (3R, 5S)-3-hydroxy-3-(4-hydroxy-3-methoxybenzyl)-5-(4-hydroxy-3-methoxyphenyl)-3,4,5,6-tetrahydro-2H-pyran-2-one having $^1$H-NMR and $^{13}$C-NMR spectrums as follows:

$^1$H NMR (500 MHz, acetone-d$_6$); $\delta$2.43(1H,m), 2.48(1H,dd,J=9.6,13.3 Hz), 2.79(1H,dd,J=4.6,13.3 Hz), 2.84(1H,d,J=13.7 Hz), 3.12(1H,d,J=13.7 Hz), 3.79(3H,s), 3.82(3H,s), 6.57(1H,dd,J=2.3,8.2 Hz), 6.59(1H,dd,J=2.3,8.2 Hz), 6.66(1H,d,J=2.3 Hz), 6.68(1H,d,J=2.3 Hz), 6.69(1H,d,J=8.2 Hz), 6.70(1H,d,J=8.2 Hz) $^{13}$C NMR (125 MHz, acetone-d$_6$); $\delta$32.2(CH$_2$), 41.8(CH$_2$), 44.6 (CH), 56.4(CH$_3$—Ox2), 71.8(CH$_2$—O), 77.4(C—O), 113.5(CH), 114.9(CH), 116.1(CH), 116.2(CH), 122,3(CH), 124.0(CH), 128.2(C), 131.9(C), 146.1(C), 146.7(C), 148.8(C), 149.0(C), 180.6(C=O).

* * * * *